(12) United States Patent
Hansson et al.

(10) Patent No.: US 6,749,594 B2
(45) Date of Patent: Jun. 15, 2004

(54) ABSORBENT PRODUCT WITH ENHANCED INCONSPICUOUSNESS

(75) Inventors: Roy Hansson, Mölndal (SE); Camilla Elfsberg, Göteborg (SE); Charlotte Persson, Göteborg (SE); Camilla Björklund, Mölnlycke (SE); Lina Strand, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 69 days.

(21) Appl. No.: 10/119,026

(22) Filed: Apr. 10, 2002

(65) Prior Publication Data

US 2002/0156446 A1 Oct. 24, 2002

Related U.S. Application Data

(60) Provisional application No. 60/282,855, filed on Apr. 11, 2001.

(51) Int. Cl.[7] .................................................. A61F 13/15
(52) U.S. Cl. ................................................ 604/385.04
(58) Field of Search ......................... 604/385.04, 385.03, 604/385.01, 386, 387

(56) References Cited

U.S. PATENT DOCUMENTS

| 4,728,325 | A | * | 3/1988 | Spiller | 604/372 |
|---|---|---|---|---|---|
| 5,501,679 | A | * | 3/1996 | Krueger et al. | 604/393 |
| 5,843,260 | A | * | 12/1998 | Huskey | 156/153 |
| 6,506,473 | B1 | * | 1/2003 | Hisanaka et al. | 428/138 |
| 6,653,523 | B1 | * | 11/2003 | McCormack et al. | 604/367 |
| 2001/0044611 | A1 | * | 11/2001 | Noda et al. | 604/367 |
| 2003/0045845 | A1 | * | 3/2003 | Yoshioka | 604/361 |

FOREIGN PATENT DOCUMENTS

| EP | 0 359 501 B1 | 3/1990 |
|---|---|---|
| EP | 0 359 501 A2 | 3/1990 |
| EP | 1 078 619 A2 | 2/2001 |
| EP | 1 110 527 A2 | 6/2001 |
| EP | 1 138 293 A1 | 10/2001 |
| WO | 98/05285 | 2/1998 |
| WO | 98/25564 | 6/1998 |

* cited by examiner

*Primary Examiner*—Weilun Lo
*Assistant Examiner*—Michael Bogart
(74) *Attorney, Agent, or Firm*—Burns, Doane, Swecker & Mathis, L.L.P.

(57) ABSTRACT

Absorbent product (101) such as a sanitary towel, a panty liner or an incontinence pad, which product has two transverse end edges (117, 118), two longitudinal side edges (119, 120), a liquid-permeable surface layer (102), a liquidtight backing layer (103) and an absorbent core (104) arranged between these layers (102, 103), the product having side flaps (106) arranged at the longitudinal side edges (119, 120) on both sides of the absorbent core (104), which side flaps (106) are of such shape and size that, during use of the product, they can be folded around the leg edges in the crotch portion on a pair of briefs, the side flaps (106) exhibiting a gloss below 25% and a regular transmittance above 5%.

16 Claims, 11 Drawing Sheets

ABSORBENT PRODUCT WITH ENHANCED INCONSPICUOUSNESS

CROSS REFERENCE TO RELATED APPLICATIONS

The present application claims the priority under 35 U.S.C. §119 of U.S. Provisional Application No. 60/282,855, filed in the United States on Apr. 11, 2001, the entire contents of which are hereby incorporated herein by reference.

TECHNICAL FIELD

Absorbent product such as a sanitary towel, a panty liner or an incontinence pad, which product has two transverse end edges, two longitudinal side edges, a liquid-permeable surface layer, a liquidtight backing layer and an absorbent core arranged between these layers, the product having side flaps arranged at the longitudinal side edges on both sides of the absorbent core, which side flaps are of such shape and size that, during use of the product, they can be folded around the leg edges in the crotch portion on a pair of briefs.

BACKGROUND ART

Modern conventional absorbent articles either have side flaps or do not. The purpose of the side flaps is to be folded around the edges of the briefs in the crotch portion and in this way help to ensure good fastening of the article in the briefs so that the article does not lie askew. An example of a document which describes the importance of side flaps for the fastening of an absorbent article is EP 0 359 501. A further reason for providing an absorbent article with side flaps is that the risk of leakage occurring is reduced. Leakage often arises in articles without side flaps when the edges of the briefs in the crotch area become folded in over the top side of the article or when the article has ended up askew in the briefs. This usually happens when the article is narrower than the width of the briefs. Leakage can also occur when the bodily fluid cannot be absorbed in time by the central portion of the article but runs out and over the side edges of the article where the bodily discharge comes into contact with the briefs. An article with side flaps ensures the positioning of the article in the briefs and reduces the occurrence of leakage. In order to reduce the leakage along the sides of the article, the article is advantageously provided with side flaps which are as long as possible along the longitudinal side edges of the article. Examples of articles with long side flaps are described in, for example, WO 98/25564 and EP 0 928 179. However, many wearers feel an article with conventional side flaps is insufficiently inconspicuous, because the side flaps are visible on the outside of the briefs. This is of course more marked, the larger the side flaps are. An article which does not have side flaps is in this respect much more discreet as no side flaps have been folded around the briefs in the crotch area. However, leakproofness is inferior in such an article. Articles without side flaps are therefore most often recommended for use when smaller flows of liquid are to be received by the article. Manufacturers of sanitary articles have traditionally used material which has a whitish colour In order to give the consumer a feeling of freshness with the article and in order to be suitable for white briefs, which has been the most common colour of briefs on the market. The market has changed now, and there is a wide variety of briefs with both different colours and different patterns, which means that white side flaps or side flaps of a colour different from that of the briefs are clearly visible on the outside of the briefs. Many people take part in sports which require a change of clothes in an environment which is to a greater or lesser extent public. In this connection, it is virtually impossible to conceal the use of a sanitary protection means with side flaps because these are visible on the outside of the briefs. The same problem arises in the case of activities such as swimming and sunbathing. There is also a requirement among some users of sanitary articles to be able to conceal the use of these in their home environment as well.

There have been attempts to solve the above problems by making the side flaps transparent. EP 1 138 293 discloses an absorbent article that shows transparent areas. However, transparency is not the same as non-visibility. The side flaps, even if they are made in a transparent material, can shine and in that way be visible. In addition, it is not necessary for the side flaps to be transparent for them to be experienced as invisible. On the contrary, a very transparent material is often very shiny.

Thus, there still is a need for an improved absorbent article with side flaps and enhanced discretion.

DISCLOSURE OF INVENTION

By means of the present invention, a product of the type referred to in the introduction has been produced, which product essentially eliminates the problems associated with previously known such products.

A product made according to the invention is principally characterized in that the side flaps exhibits a gloss below 25% and a regular transmittance above 5%. By making the side flaps exhibit a gloss below 25% and a regular transmittance of above 5%, enhanced inconspicuousness is achieved for the wearer on occasions when the wearer is seen wearing only patterned and/or coloured briefs, or sun clothes, without forgoing the leakproofness of the article, Preferably, the side flap exhibit a gloss between 3 and 10%. Most preferred is a gloss of 6%. Gloss is measured according to ASTM 2457-97. What is measured is how the material reflects light. The side flaps are experienced as being invisible when the gloss of the material in the side flaps is below 25%, provided that the material is transparent enough. Perforating the side flaps would affect the gloss so that it is decreased. However, it is difficult to measure gloss using the above method on a material that has a lot of holes. A material with a nominal value of gloss that is higher than acceptable, can be chosen if it is later perforated. The relationship between the gloss of a non-perforated material and the same material perforated, can be presumed to be linear as a function of the nominal gloss of the material. If a non-perforated piece of material has a gloss of a certain value, and that piece of material is perforated, the piece of material obtains a gloss that is a function of the starting gloss value and the open area of the perforated piece of material. That is, perforated materials are also a part of the invention. The starting point is as described above, the gloss of a non-perforated piece of material. The open area that the piece of material achieves when it is perforated then reduces that value. The value of gloss of the perforated material can be described by the following equation:

$$G_p = G_o \times f[(A_{tot} - A_{hole})/A_{tot}]$$

Where
$G_p$=gloss of the perforated material
$G_o$=gloss of the non-perforated material
f=a linear function
$A_{tot}$=total area of the piece of material
$A_{hole}$=total area of holes of the piece of material A material with a gloss that is higher then acceptable can also be chosen if it is later embossed. The gloss of an embossed material is not difficult to measure. A laminate comprising an upper perforated layer and a lower nonperforated layer is also readily measurable.

A higher gloss of the side flaps than 25% would be acceptable, or even desirable, in cases where very glossy briefs are used, such as specific types of polyester or silk. However, this type of underwear is a minority of the underwear existing and that area is not the subject for this invention.

According to a preferred embodiment of the invention, the side flaps exhibits a transmittance of above 10%. It can be preferred to make the side flaps in a material that has a regular transmittance below 90%. Above this value of the regular transmittance, a material often exhibits too high gloss to be experienced as invisible compared to a material having a regular transmittance below this value. The transmittance is measured according to ASTM D 1746-97, on a non-perforated piece of material.

According to a preferred embodiment of the invention, the side flaps are constituted by the liquidtight-backing layer which extends beyond the longitudinal side edges of the product. In this connection, a liquidtight transparent backing layer can be treated in the area of the absorbent core so that the surface within this area has greater opacity, that is to say is less transparent. The liquidtight transparent material can, for example, be coloured, provided with a colour print or stamped so that the material becomes less transparent. Such treatment may be desirable given that some users find it off putting when it is possible to see into the core of the absorbent article. This problem is especially marked when the absorbed bodily liquid is reddish menstrual fluid.

According to another embodiment, the article has been provided with an opaque layer on that side of the absorbent core which faces away from the wearer during use. This layer can be constituted by an opaque fastening means in the form of adhesive fastening glue, a mechanical fastening means or a separate layer in the form of an opaque nonwoven material, plastic layer, laminate or the like. According to a fourth embodiment, the side flaps consist of a separate material layer or laminate which is positioned and attached across the article on the inside or the outside of the liquidtight backing layer. According to a further embodiment, the side flaps consist of at least two separate material layers which are attached to the longitudinal side edges of the article. It has also been found to be advantageous if the transparent side flaps also have an adhesive fastening means adjacent to the outer contour line of the side flap in order to bring about good contact with the briefs so that the side flap does not hang down from the briefs and thus become conspicuous.

BRIEF DESCRIPTION OF FIGURES

The invention will be described in greater detail below with reference to the figures which are shown in the accompanying drawings.

DETAILED DESCRIPTION OF PREFERRED EMBODIMENTS

According to the invention, the material for the side flaps shall exhibit a gloss below at least 25%. Below that value, the material does not exhibit a disturbing gloss that would make the material visible even if it were completely transparent. The material is experienced as invisible. The gloss of a material is measured, according to the invention, by measuring the regular reflection of light. The flux of the regular reflection is divided by the flux of incident light and the result is measured in % as regular reflection. The method of measurement used here is "Standard Test Method for Specular Gloss of Plastic Films and Solid Plastics", ASTM D 2457-97. The angle (gloss angle) that is described under Section 1 "Scope" in the method can be chosen to be 20, 45 or 60°. In the measurements according to the invention the angle was chosen to be 60°. The measurements were made on non-perforated materials.

As earlier described, it is important that the side flaps are to a certain extent transparent for them to be experienced as invisible. However, as described above, very high transparency is often associated with high gloss. The transparency necessary for the invention is measured according to the method "Standard Test Method for Transparency of Plastic Sheeting", ASTM D 1746-97. According to this method, regular transmittance of light is measured. Regular transmittance is the result of the flux of regularly transmitted light divided by the flux of incident light. Regular transmittance is given in %. The measurements were made on non-perforated materials.

Figure 1:
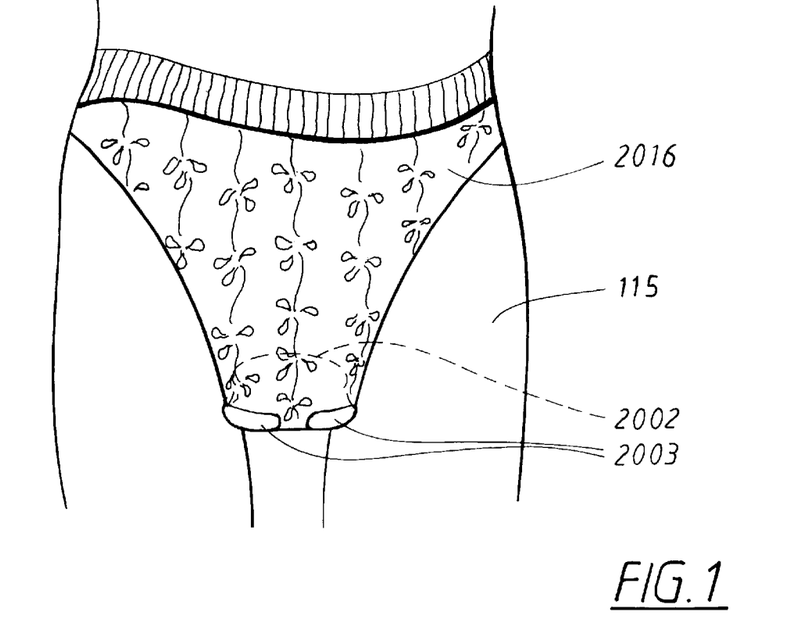
FIG. 1 shows a wearer from the front wearing a conventional sanitary towel provided with side flaps inside a pair of briefs.
Figure 2:
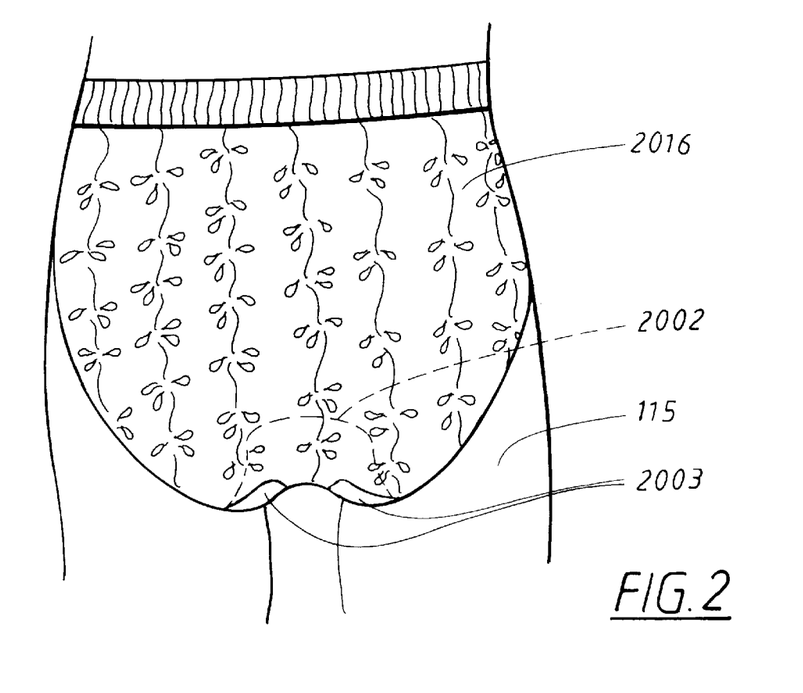
FIG. 2 shows a wearer from the rear wearing a conventional sanitary towel provided with side flaps inside a pair of briefs.

In the examples, absorbent products in the form of sanitary towels are described, but the invention can of course be applied to panty liners or incontinence pads. FIGS. 1 and 2 show a wearer 115 seen from the front and, respectively, from the rear, wearing a conventional sanitary towel 2002 inside a pair of briefs 2016. The sanitary towel has been designed with side flaps 2003 which have been folded around the edges of the briefs. The side flaps 2003 of the sanitary towel are clearly visible on the outside of a pair of briefs 2016 when these have a colour and/or pattern different from that of the side flaps 2003.

Figure 3:
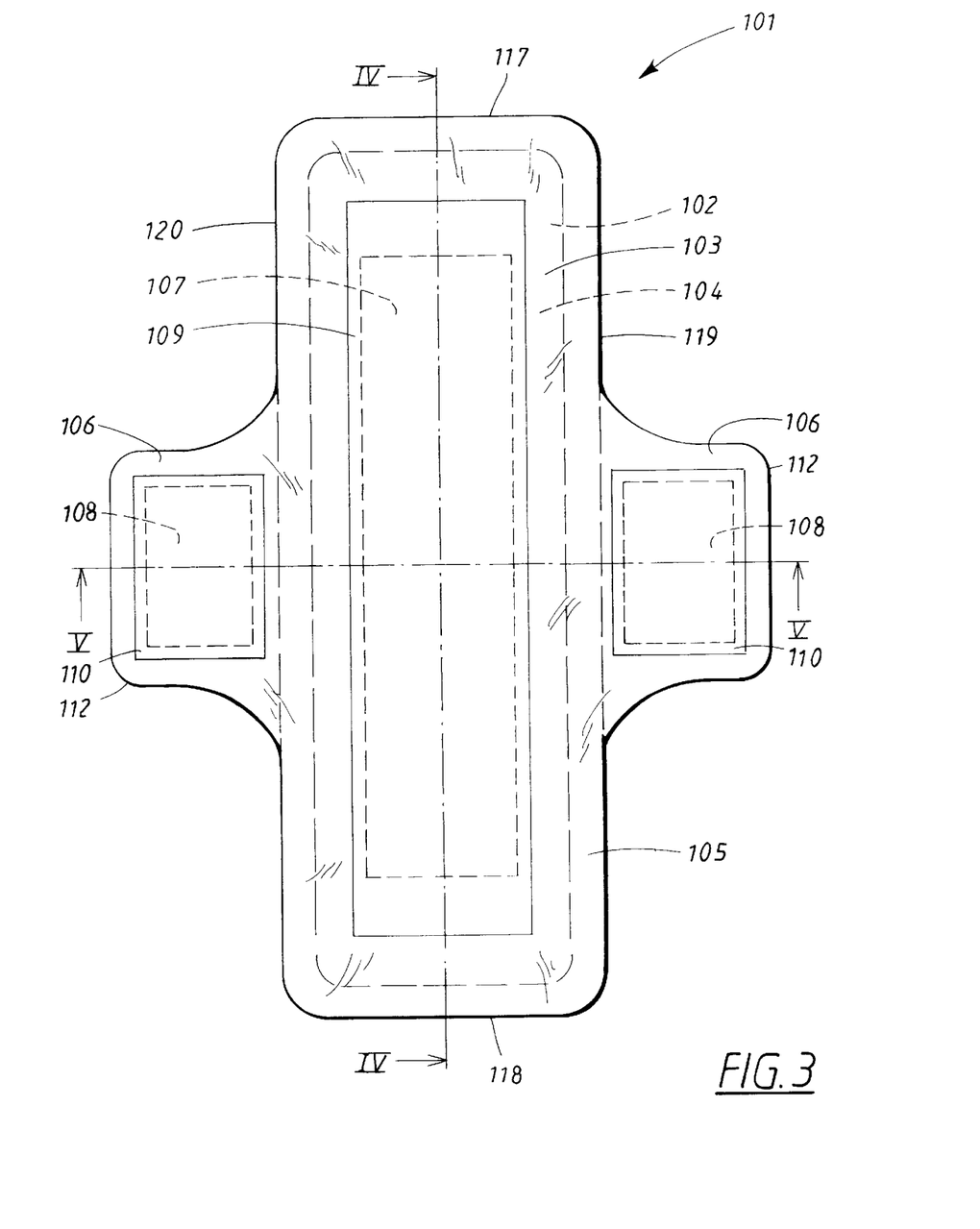
FIG. 3 shows a sanitary towel, seen from the side which is to face the briefs during use.
Figure 4:
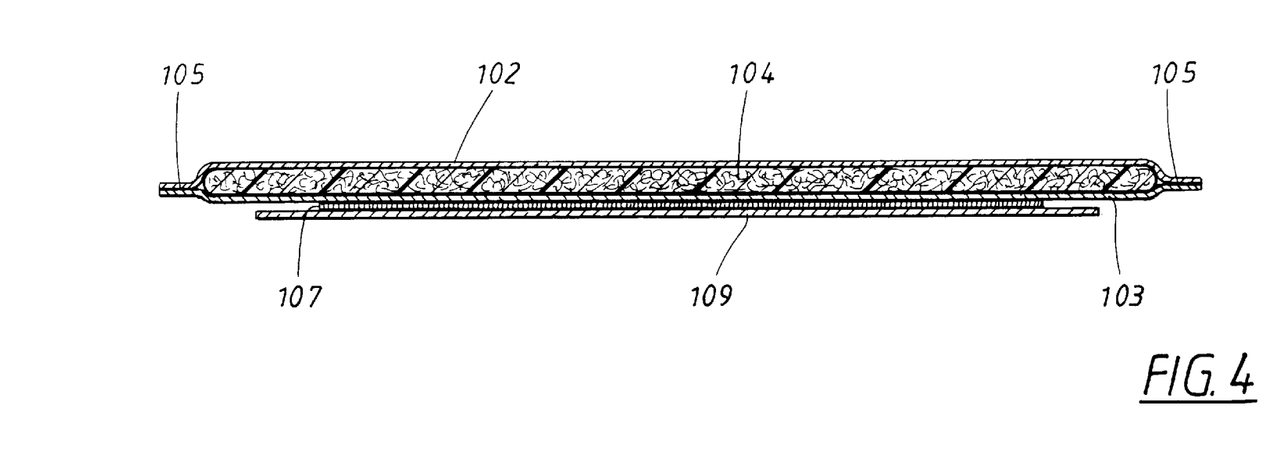
FIG. 4 shows a section along the line IV—IV through the sanitary towel in FIG. 3.
Figure 5:
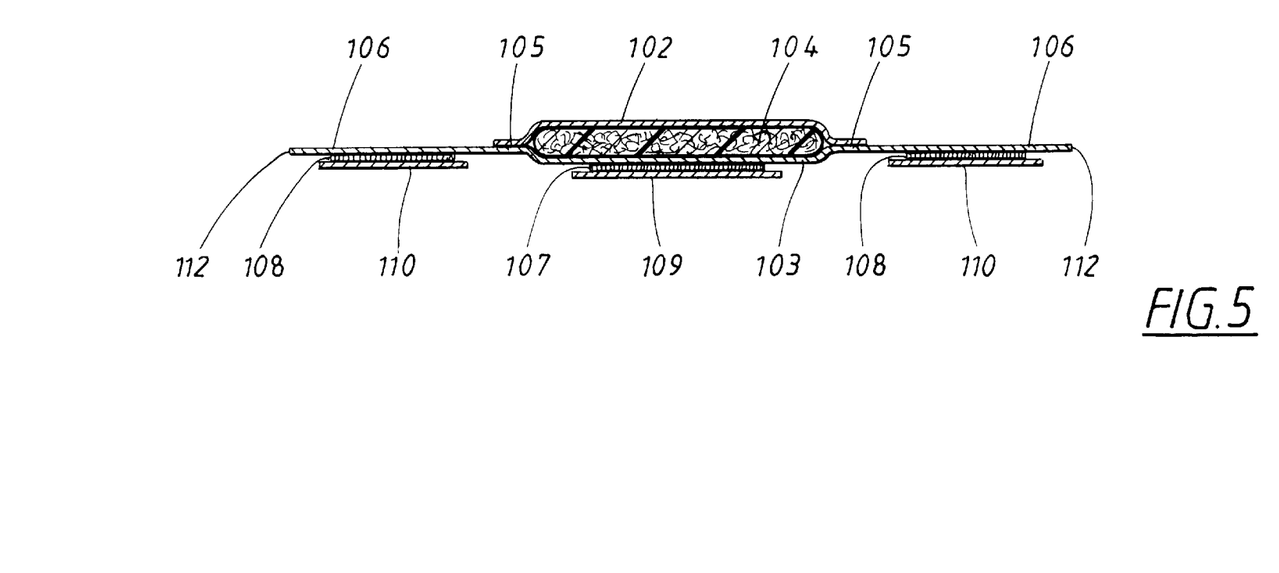
FIG. 5 shows a section along the line V—V through the towel in FIG. 3.

FIGS. 3–5 show a sanitary towel 101 seen from the side which is intended to face the underwear of the wearer during use, which sanitary towel 101 has two transverse end edges 117, 118 and two longitudinal side edges 119, 120. FIG. 3 shows a sanitary towel, seen from the side which is to face the briefs during use, FIGS. 4 and 5 show sections through the sanitary towel in FIG. 3. A liquid-permeable surface layer 102 is arranged on that side of the sanitary towel which is intended to face the wearer. The liquid-permeable surface layer 102 suitably consists of a soft, skin-friendly material. Examples of suitable liquid-permeable materials are various types of non-woven fabrics. Another example of a liquid-permeable material is a layer of continuously longitudinal fibres. Other possible liquid-permeable materials are perforated plastic films, not, knitted or woven textiles and combinations and laminates of the material types listed.

The sanitary towel 101 also comprises a liquidtight backing layer 103 arranged on that side of the sanitary towel which is to face away from the wearer. In the illustrative embodiment shown, a thin transparent flexible plastic film is used as the liquidtight-backing layer 103. Examples of suitable films are natural polypropylene and polyethylene films or laminates of these. The word natural means films without added organic or inorganic pigments, for example titanium dioxide.

Positioned between the liquid-permeable surface layer 102 and the liquidtight backing layer 103 is an absorbent core 104 which can comprise one or more material layers. A suitable material for the absorbent core 104 is, for example, cellulose pulp. This may be in the form of rolls, bales or sheets which are dry-defibred and converted in fluffed form into a pulp mat, with what are known as superabsorbents, which are polymers with the capacity to absorb several times their own weight of water or bodily fluid, being mixed in if so desired. Examples of other usable materials are various types of regenerated cellulose, for example viscose fibres as described in SE 9903070-2. Natural fibres such as cotton fibres, peat or the like can also be used. It is of course also possible to use absorbent and/or hydrophilic synthetic fibres or mixtures of natural fibres and synthetic fibres.

The two layers, the liquid-permeable surface layer 102 and the liquidtight backing layer 103, are interconnected and form a projecting edge connection 105 around the longitudinal side edges 119, 120 and the transverse end edges 117, 118 of the sanitary towel. The connection can be made by any known technique suitable for the purpose, such as gluing, welding or sewing.

The sanitary towel also has two transparent side flaps 106 arranged on either side of the absorbent core 104, the side flaps 106 projecting in the transverse direction from each longitudinal side edge 119, 120. The side flaps 106 are of such shape and size that, during use, they can be folded around the leg openings of the briefs. In this embodiment, the side flaps 106 are constituted by the liquidtight backing layer 103. A fastening means 107 is arranged on that surface of the liquidtight backing layer 103 facing away from the wearer, in the area of the absorbent core 104. In this embodiment, the fastening means 107 is an adhesive means which is protected by a removable protective layer 109. The protective layer 109 is intended to protect the adhesive fastening means 107 from dirt and dust and to prevent the glue from adhering in an undesirable manner to other surfaces or to itself until the sanitary towel is to be used. As an alternative to the adhesive fastening means 107, use can be made of a means which has mechanical adhesion or high friction properties, such as touch and close material or foamed material. When a touch and close material or a foamed material is used as the fastening means, the protective layer 109 can be omitted. The projecting side flaps 106 have also been provided with fastening means 108 on the surface facing away from the wearer in order to ensure that the side flaps 106 make good contact against the outside of the briefs during use. The fastening means 108 is suitably constituted by a transparent adhesive fastening glue which is protected by removable protective layers 110.

According to another embodiment (not shown in the figures), the sanitary towel has a liquidtight backing layer 103 which has been treated so that it is opaque in the area of the absorbent core 104 in order to reduce the visibility of the absorbent core. Increased opacity can be brought about by the plastic film being coloured by, for example, titanium dioxide, or by the surface being finished mechanically so that the surface reflects light differently, its opacity then being increased, Another way of providing protection against the absorbent core 104 being visible through the liquidtight backing layer 103 of the sanitary towel is by arranging the fastening means 107 as a covering coating and by colouring it so that a layer with an opaque effect is obtained.

Figure 6:
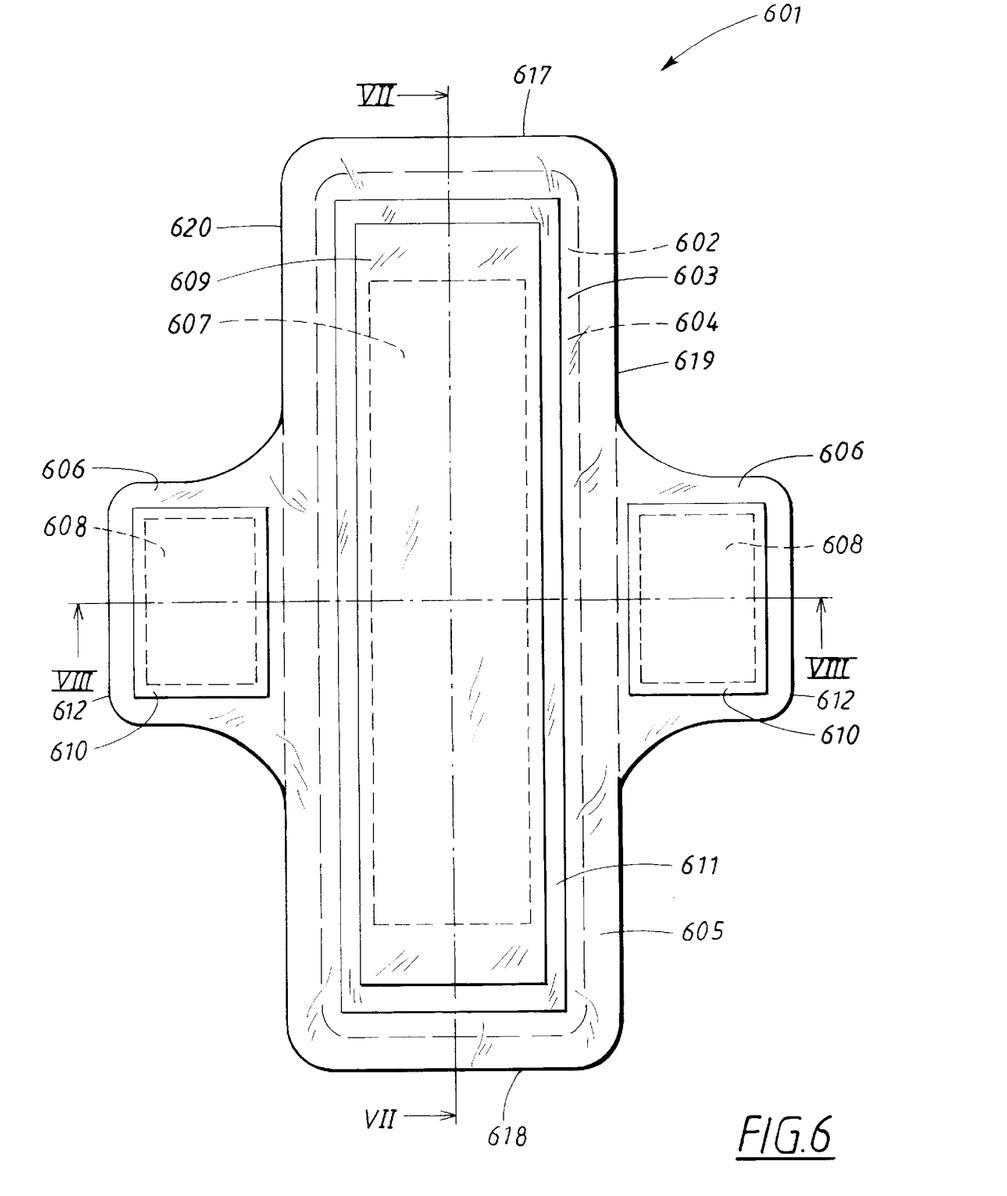
FIG. 6 shows a sanitary towel according to another embodiment of the invention, seen from the side which is to face the briefs during use.
Figure 7:
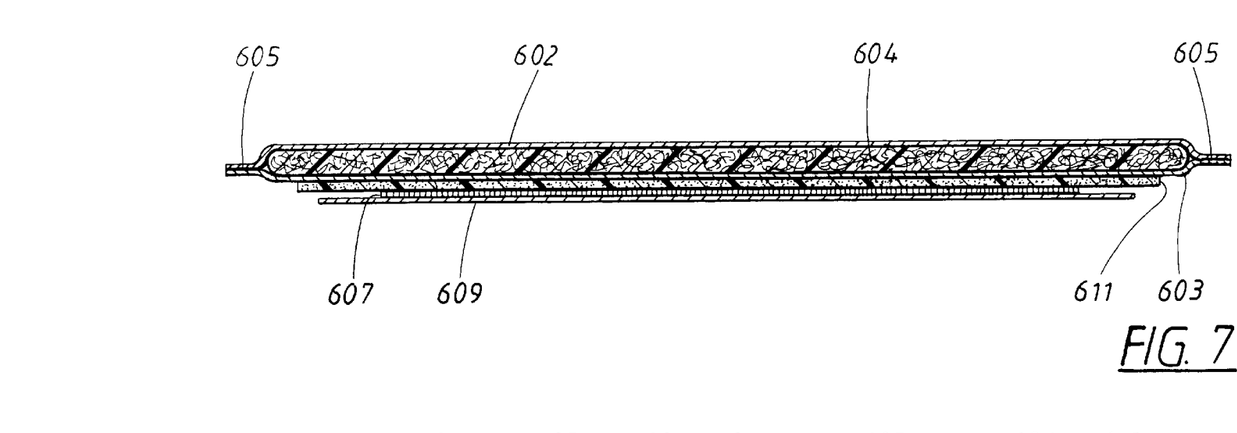
FIG. 7 shows a section along the line VII—VII through the sanitary towel in FIG. 6.
Figure 8:
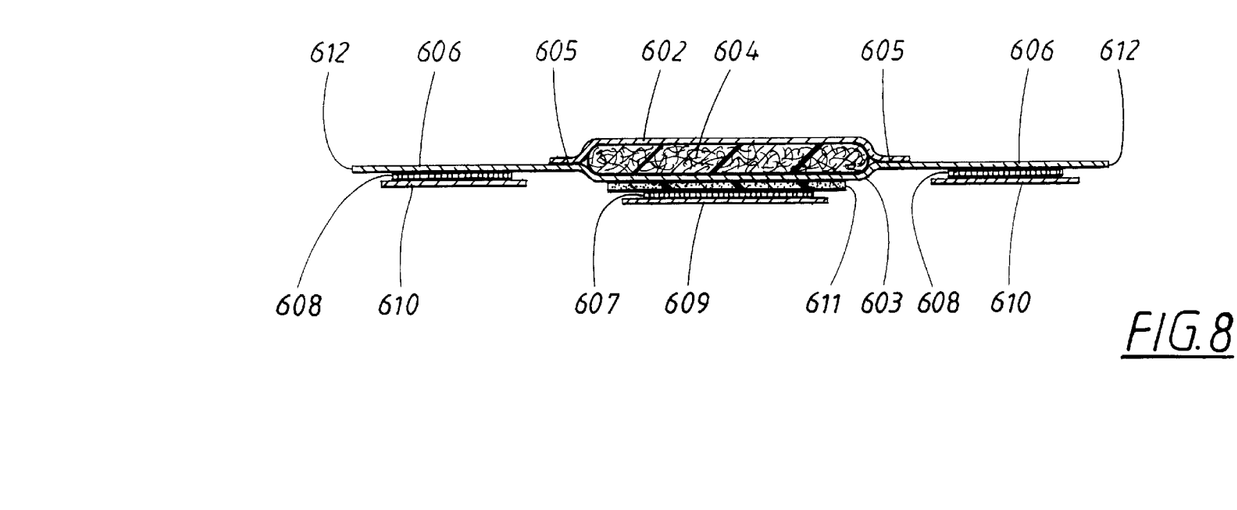
FIG. 8 shows a section along the line VIII—VIII through the sanitary towel in FIG. 6.

FIGS. 6–8 show a sanitary towel 601 of fundamentally the same construction as the sanitary towel in FIGS. 3–5. The numbering of the different parts of the sanitary towel in FIGS. 6–8 is therefore by analogy with that used in the description of the sanitary towel in FIGS. 3–5. However, the sanitary towel 601 shown in FIG. 6 does differ in one respect from the sanitary towel 101 described previously.

The sanitary towel 601 has protection 611 against the absorbent core 604 being visible brought about by virtue of an opaque material layer 611 having been positioned in the area of the absorbent core 604 on that side of the liquidtight backing layer 603 which faces away from the wearer. The opaque material layer 611 can consist of, for example, an opaque non-woven material, cellulose layer, plastic material or laminate of said materials. It is of course also possible to position the opaque material layer 611 on the inside of the liquidtight backing layer 603 between the absorbent core 604 and the liquidtight backing layer 603. The opaque material layer 611 preferably consists of a hydrophobic material, for example a coloured film, when the opaque material layer 611 is positioned between the absorbent core 604 and the liquidtight backing layer 603.

Figure 9:
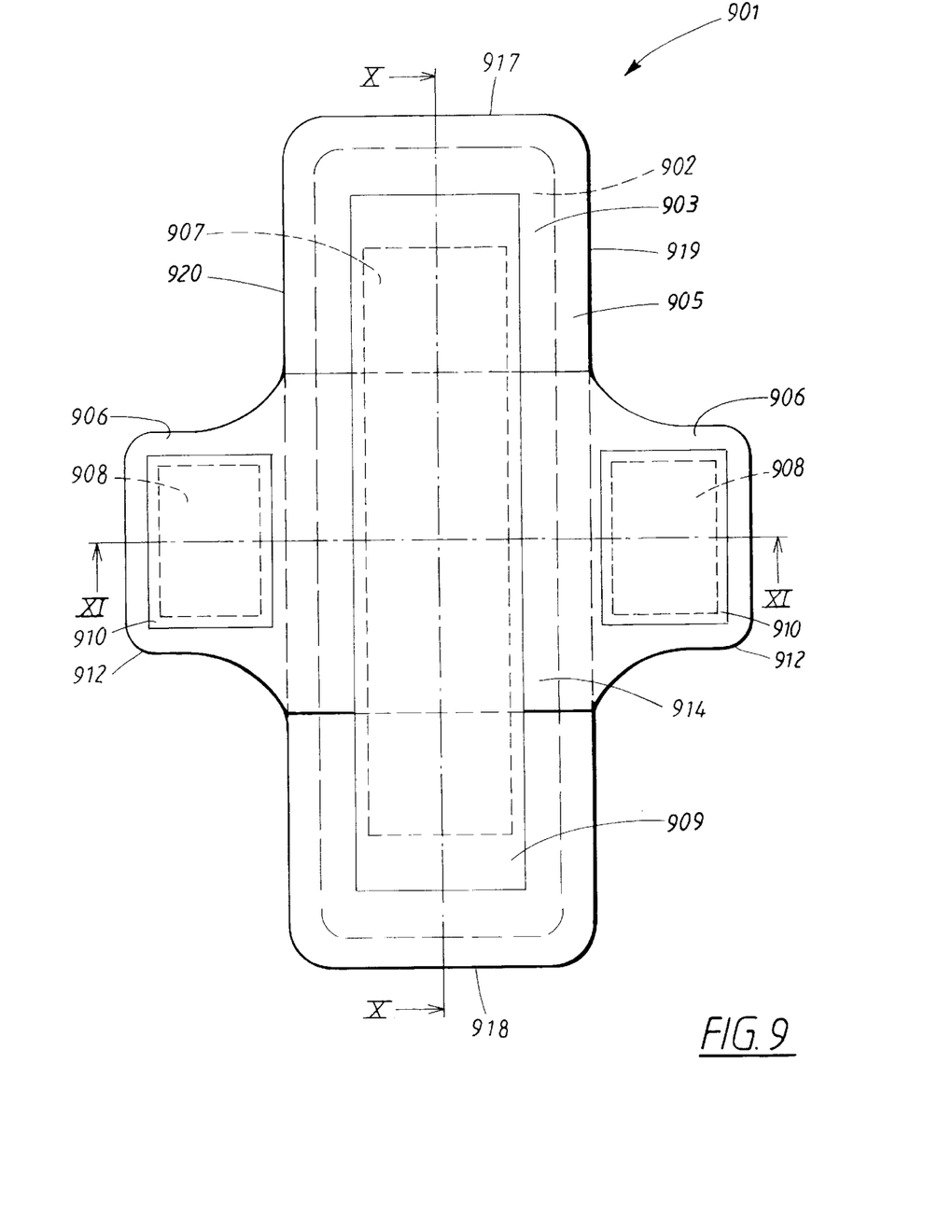
FIG. 9 shows a sanitary towel according to another embodiment of the invention, seen from the side which is to face the briefs during use.
Figure 10:
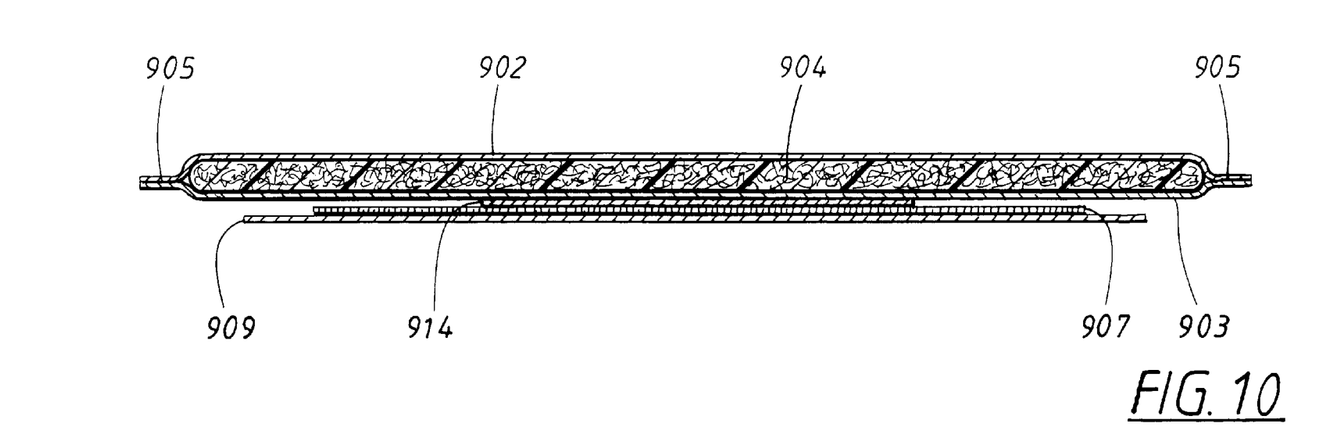
FIG. 10 shows a section along the line X—X through the sanitary towel in FIG. 9.
Figure 11:
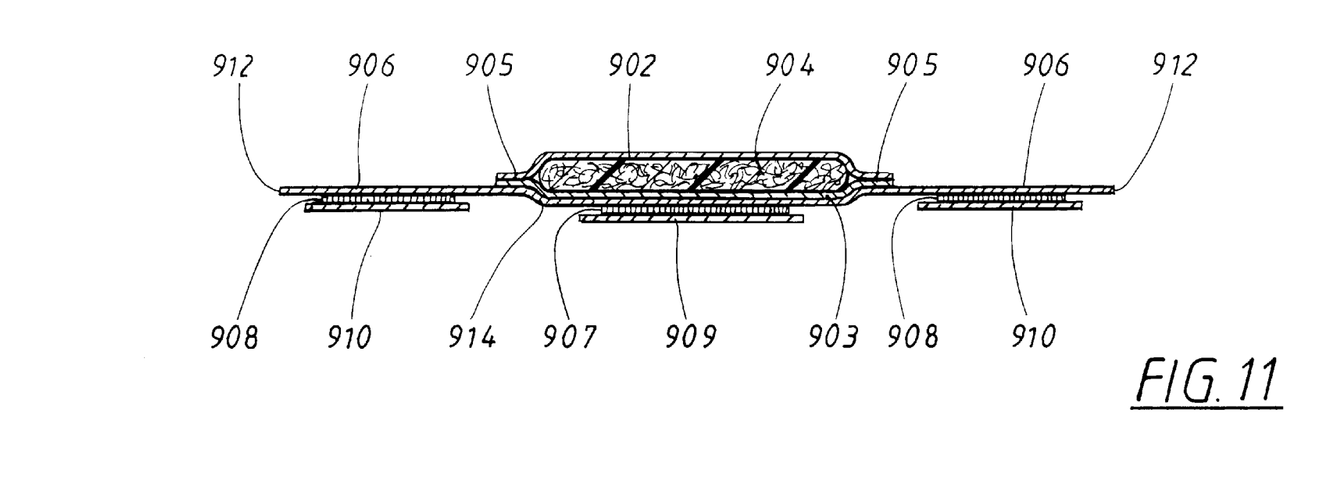
FIG. 11 shows a section along the line XI—XI through the sanitary towel in FIG. 9.
Figure 12:
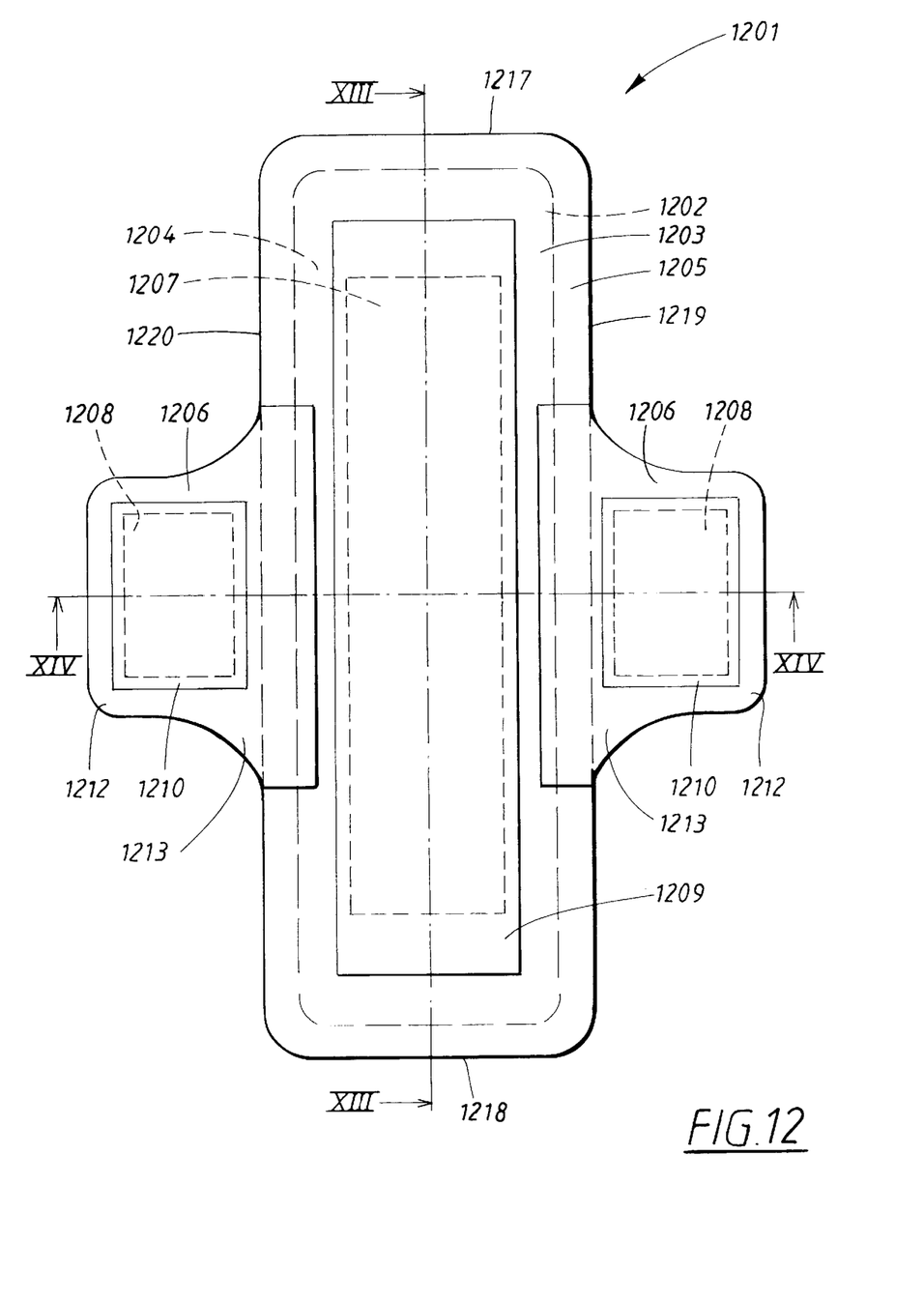
FIG. 12 shows a sanitary towel according to a further embodiment of the invention, seen from the side which is to face the briefs during use.
Figure 13:
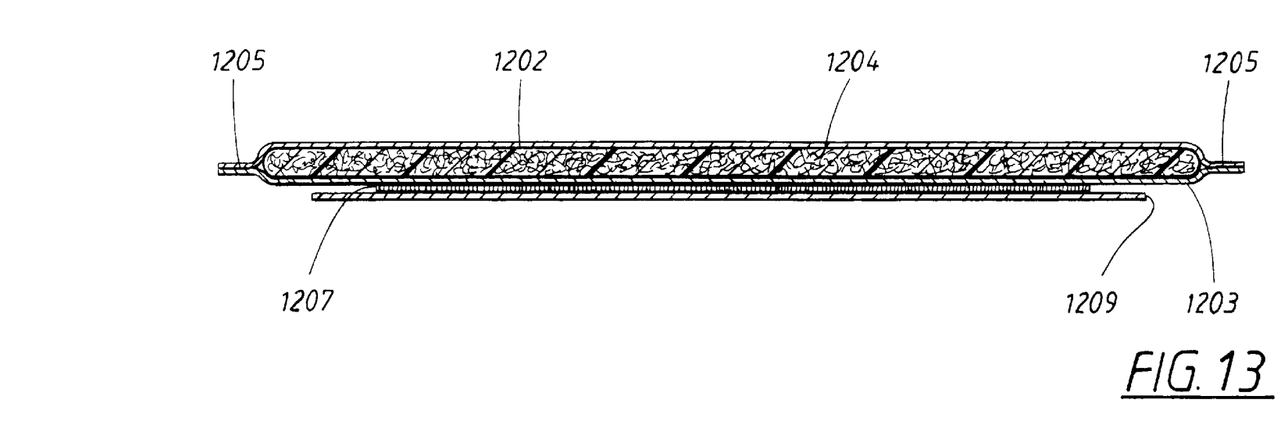
FIG. 13 shows a section along the line XIII—XIII through the sanitary towel in FIG. 12.
Figure 14:
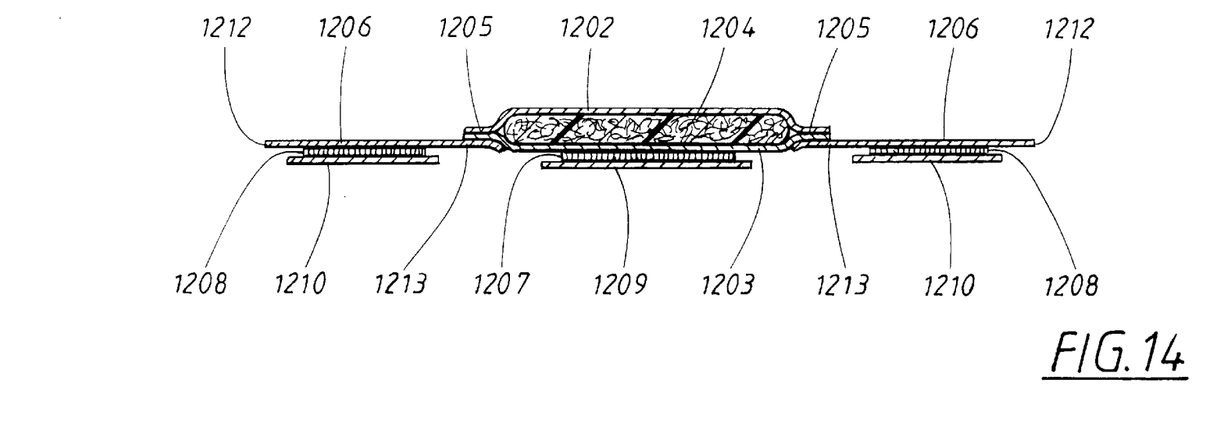
FIG. 14 shows a section along the line XIV—XIV through the sanitary towel in FIG. 12.

FIGS. 9–11 show another variant of the invention. Like the sanitary towel shown in FIGS. 3–5, the sanitary towel 901 in FIGS. 9–11 is constructed in a conventional manner, with an absorbent core 904 enclosed between a liquid-permeable surface layer 902 and a liquidtight backing layer 903. The two layers, the liquid-permeable surface layer 902 and the liquidtight backing layer 903, are interconnected and form a projecting edge connection 905 around the longitudinal side edges 919, 920 and the transverse end edges 917, 918 of the sanitary towel. A fastening means 907 is also arranged on that, surface of the liquidtight backing layer 903 facing away from the wearer, in the area of the absorbent core 904. The fastening means 907 is protected by a removable protective layer 909. The side flaps 906 are constituted by a transparent material layer 914 which has been positioned across the sanitary towel 901 on that side of the liquidtight backing layer 903 which faces away from the wearer. The material layer 914 has been positioned in such a manner that it projects beyond the longitudinal side edges 919, 920 of the sanitary towel and forms the side flaps 906. The separate transparent material layer 914 consists of, for example, transparent polyethylene film, polypropylene film or a laminate of these. For increased breathability of the product, it is an advantage if the material layer is made of a breathable material, for example a microporous, air-permeable film. This can be made of various materials, for example polyethylene or polypropylene. The advantage of this embodiment is that it affords a greater range of options for selecting from a large number of materials for the liquidtight backing layer 903 as the choice does not depend on the choice for the material layer 914. For example, the liquidtight backing layer 903 can be a simple opaque non-woven materials, and the material layer 914 can be a transparent, liquidtight but breathable material. This produces a sanitary towel with increased comfort because a maximum surface area with air-permeability is obtained, at the same time as a sufficiently liquid-impermeable surface underneath the absorbent core 904 is obtained in the area of the material layer 914 in the crotch area. The connection between the transparent material layer 914 and the liquidtight backing layer 903 can be made by any known technique suitable for the purpose, such as gluing, welding or sawing.

The sanitary towel 1201 shown in FIGS. 12–15 is on the whole constructed in the same manner as the sanitary towel in FIGS. 9–11. The major difference is that the side flaps 1206 consist of two separate transparent material layers 1213 which are attached to the liquidtight backing layer 1203. These separate transparent material layers 1213 are advantageously attached to the liquidtight backing layer 1203 at the same time as the connection 1205 is made between the liquidtight backing layer 1203 and the liquid-permeable surface layer 1202 along the longitudinal side edges 1219, 1220 of the article.

FIGS. 15–18 show examples of the distribution of the transparent adhesive fastening glue 1508 on the side flap 1506. It has been found that it is significant that the transparent side flap 1506 has adhesive fastening glue 1508 which extends adjacent to the outer contour line 1512 of the side flap 1506 in order to bring about good contact between the outer contour line 1512 of the side flap 1506 and the briefs so that the side flap 1506 is prevented from hanging down or being bent out from the outside of the briefs and thus becoming conspicuous. The glue can extend so far that it coincides with the outer contour line 1512 of the side flap 1506. In order that good contact of the side flap 1506 against the briefs is obtained, the extent of the glue should not be less than 5 mm from the outer contour line 1512 of the side flap 1506.

A protective layer 1510 is positioned over the transparent adhesive fastening glue 1508. This protective layer 1510 has release properties on at least the side which faces the adhesive fastening glue 1508, in order to protect the latter against dirt and dust and to prevent the glue from adhering in an undesirable manner to other surfaces or to itself until the sanitary towel is to be used.

Figure 15:
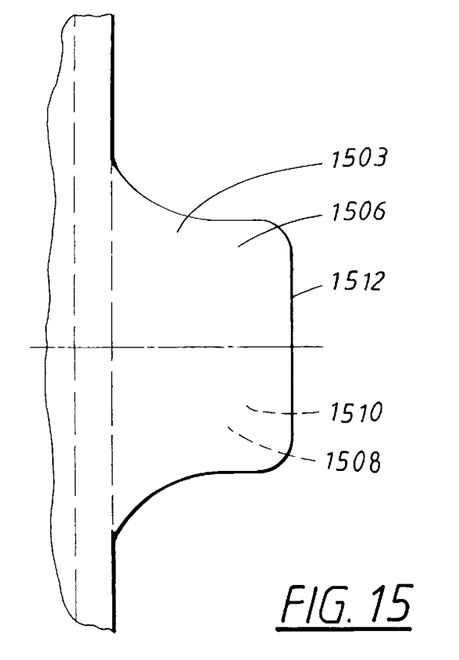
FIGS. 15–18 show proposed designs of the fastening means on the side flaps.
Figure 16:
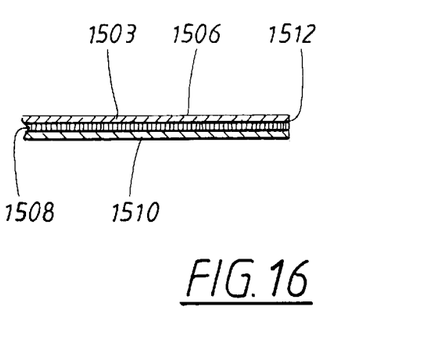
Figure 17:
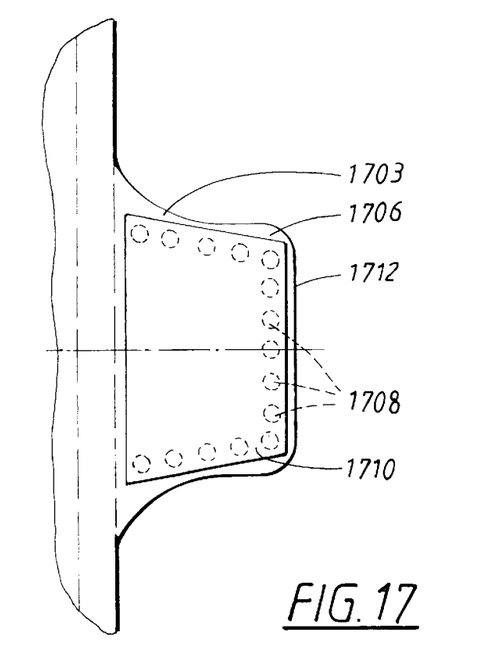
Figure 18:
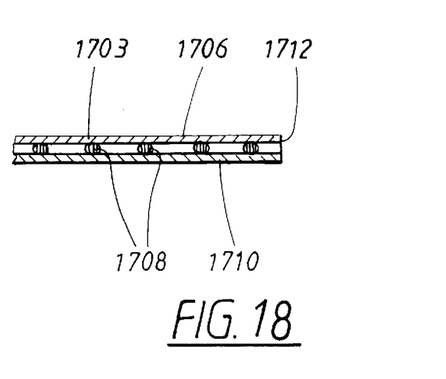

FIGS. 15 and 16 illustrate a side flap 1506 which has been coated with an adhesive fastening glue 1508 over the entire surface of the side flap on the side which is intended to be attached to the outside of the briefs during use. FIGS. 17 and 18 show a side flap 1706 which has been coated with an adhesive fastening glue 1708 only close to the outer contour line 1712 of the side flap in the form of spots. The adhesive fastening glue 1508 can of course be applied in different patterns and extents as long as the conditions mentioned above for good contact of the side flap 1706 against the briefs are satisfied.

Figure 19:
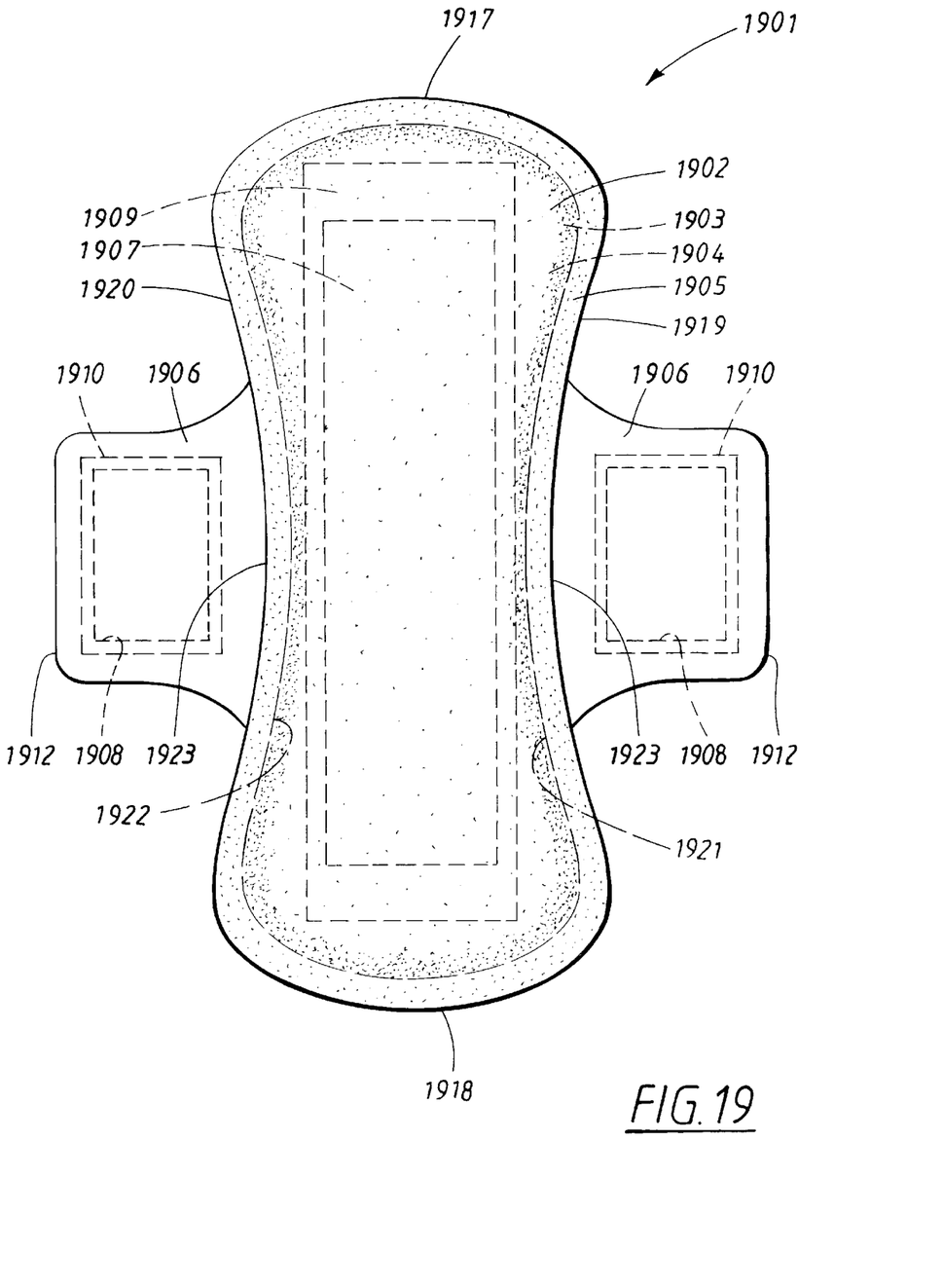
FIG. 19 shows a sanitary towel with an hourglass-shaped absorbent core, seen from the side which is to face the wearer during use.

FIG. 19 shows a sanitary towel 1901 seen from the side which is to face the wearer during use. The sanitary towel 1901 is of fundamentally the same construction as the sanitary towels 101, 601, 901 and 1201 illustrated in previous figures. The numbering of the different parts of the sanitary towel in FIG. 19 is therefore by analogy with that used in the description of the sanitary towels 101, 601, 901 and 1201 in the previous figures. However, the sanitary towel 1901 shown in FIG. 19 differs in two respects from the sanitary towels 101, 601, 901 and 1201 described previously.

The sanitary towel 1901 shows an example of a sanitary towel with an hourglass-shaped absorbent core 1904. By giving the absorbent core 1904 an hourglass shape, the sanitary towel can be afforded better contact against the thighs of the wearer and thus improved comfort during use of the sanitary towel 1901. The sanitary towel 1901 has also been designed with a liquid-permeable surface layer 1902 which has a shape which follows the contour of the longitudinal edges 1921, 1922 of the absorbent core at least in the area of the crotch portion 1923. By designing the liquid-permeable surface layer 1902 so that it follows the longitudinal edges 1921, 1922 of the absorbent core, an aesthetically improved sanitary towel is obtained.

The invention is not to be considered as being limited by the illustrative embodiments described here. All possible combinations and variants of the illustrative embodiments described are also intended to be included within the scope of the invention.

What is claimed is:

1. An absorbent product comprising: two transverse end edges, two longitudinal side edges, a liquid-permeable surface layer, a liquidtight backing layer and an absorbent core arranged between these layers, side flaps arranged at the longitudinal side edges on both sides of the absorbent core, which side flaps are of such shape and size that, during use of the product, they can be folded around leg edges of a pair of briefs in a crotch portion of the pair of briefs, wherein the side flaps exhibit a gloss below 25% and a regular transmittance above 5%.

2. An absorbent product according to claim 1, wherein the side flaps exhibit a gloss between 3 and 10%.

3. An absorbent product according to claim 1, wherein the side flaps exhibit a regular transmittance above 10%.

4. An absorbent product according to claim 1, wherein the side flaps are formed by the liquidtight backing layer.

5. An absorbent product according to claim 4, wherein the liquidtight backing layer consists of a transparent breathable microporous film.

6. An absorbent product according to claim 4, wherein the liquidtight backing layer has been treated in an area of the absorbent core so that this area has a surface which is not transparent.

7. An absorbent product according to claim 1, wherein the product is provided with an opaque layer attached to the liquidtight backing layer.

8. An absorbent product according to claim 7, wherein the opaque layer is an opaque non-woven layer, plastic layer, cellulose layer or laminate.

9. An absorbent product according to claim 7, wherein the opaque layer is a non-transparent fastening means.

10. An absorbent product according to claim 9, wherein the opaque layer is a coloured fastening glue.

11. An absorbent product according to claim 1, wherein the side flaps comprise a separate material layer.

12. An absorbent product according to claim 11, wherein the separate material layer is attached to the liquidtight backing layer.

13. An absorbent product according to claim 1, wherein the side flaps comprise at least two separate material layers which are attached to the longitudinal side edges of the product.

14. An absorbent product according to claim 1, wherein the side flaps have a transparent fastening means which follows an outer contour line of the side flap on a side of the side flap which faces the briefs during use.

15. An absorbent product according to claim 1, wherein the liquid-permeable surface layer follows a contour of the absorbent core at least in an area of a crotch portion of the product.

16. An absorbent product according to claim 1, wherein the product is a sanitary towel, a panty liner, or an incontinence pad.

* * * * *